United States Patent [19]
Redfern et al.

[11] Patent Number: 5,843,034
[45] Date of Patent: Dec. 1, 1998

[54] HYPODERMIC SYRINGE WITH RETRACTABLE NEEDLE MOUNT

[75] Inventors: Robert Roy Redfern, deceased, late of Preston, by Elaine Redfern executrix; Elaine Redfern, Preston; Jon James Van Noorden; Fleur Denise Van Noorden, both of Eltham, all of Australia

[73] Assignee: Lok-Tek International Ltd., Australia

[21] Appl. No.: 637,729

[22] PCT Filed: Oct. 28, 1994

[86] PCT No.: PCT/AU94/00660

§ 371 Date: Jan. 17, 1997

§ 102(e) Date: Jan. 17, 1997

[87] PCT Pub. No.: WO95/11713

PCT Pub. Date: May 4, 1995

[30] Foreign Application Priority Data

Oct. 28, 1993 [AU] Australia .................. PM2053

[51] Int. Cl.⁶ .................................... A61M 5/00
[52] U.S. Cl. ............................ 604/110; 604/195
[58] Field of Search .................... 604/110, 195, 604/187, 192, 197, 198, 218, 220, 225, 226, 263

[56] References Cited

U.S. PATENT DOCUMENTS

| | | |
|---|---|---|
| 4,026,287 | 5/1977 | Haller . |
| 4,507,117 | 3/1985 | Vining et al. . |
| 4,592,744 | 6/1986 | Jagger et al. . |
| 4,650,468 | 3/1987 | Jennings, Jr. . |
| 4,675,005 | 6/1987 | DeLuccia . |
| 4,710,170 | 12/1987 | Haber et al. . |
| 4,747,829 | 5/1988 | Jacob et al. . |
| 4,747,830 | 5/1988 | Gloyer et al. . |
| 4,770,655 | 9/1988 | Haber et al. . |

(List continued on next page.)

FOREIGN PATENT DOCUMENTS

| | | |
|---|---|---|
| A-40910/85 | 10/1985 | Australia . |
| A-14189/88 | 10/1988 | Australia . |
| A-39180/89 | 2/1991 | Australia . |
| A-57097/90 | 2/1991 | Australia . |
| B-66490/90 | 7/1991 | Australia . |
| PCT/AU94/00660 | 10/1994 | Australia . |
| PCT/FR91/05304 | 4/1991 | France . |
| PCT/GB92/00652 | 4/1992 | United Kingdom . |
| WO 89/09075 | 10/1989 | WIPO . |
| WO 90/04066 | 4/1990 | WIPO . |
| WO 90/07948 | 7/1990 | WIPO . |
| WO 91/04066 | 4/1991 | WIPO . |
| WO 93/12830 | 7/1993 | WIPO . |

*Primary Examiner*—Wynn Wood Coggins
*Assistant Examiner*—A. T. Nguyen
*Attorney, Agent, or Firm*—Karen Lee Orzechowski; Nath & Associates

[57] ABSTRACT

A hypodermic syringe (10) comprising a barrel (14) for containing medicament or other liquid, movable piston means (16) including a shaft (40) provided with a chamber (42) and frangible chamber sealing means (20), needle mounting means (22) disposable within barrel (14), spring means (18) for imparting movement to needle mounting means (22), and restraining means (28) in barrel (14) comprising an annular structure (36) located towards first end (30) of barrel (14) extending inwardly thereof and containing a plurality of radially-extending weakened portion (38), wherein needle mounting means (22) when in a first position extends partway from first end (30) and is restrained from movement by engagement with restraining means (28), the restraining means (28) being operable to release needle mounting means (22) when piston (16) approaches first end (30) and then to engage and restrain piston (16) from reverse movement, the needle mounting means (22) on release having been propelled through frangible diaphragm (66) to a second position wherein it is received and retained within chamber (42) in a jamming relationship.

14 Claims, 6 Drawing Sheets

U.S. PATENT DOCUMENTS

| | | |
|---|---|---|
| 4,838,869 | 6/1989 | Allard . |
| 4,966,593 | 10/1990 | Lennox . |
| 4,994,034 | 2/1991 | Botich et al. .......................... 604/110 |
| 5,049,133 | 9/1991 | Villen Pascual . |
| 5,064,419 | 11/1991 | Gaarde . |
| 5,114,410 | 5/1992 | Caralt Batile . |
| 5,180,369 | 1/1993 | Dysarz . |
| 5,180,370 | 1/1993 | Gillespie . |
| 5,385,551 | 1/1995 | Shaw . |
| 5,407,436 | 4/1995 | Toft et al. .............................. 604/110 |
| 5,487,732 | 1/1996 | Jeffrey ................................. 604/195 X |

FIG. 6
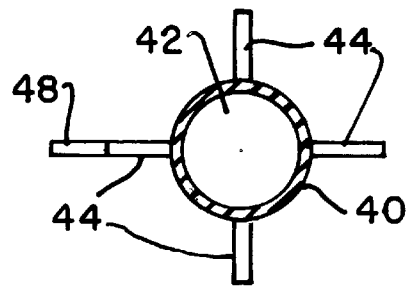
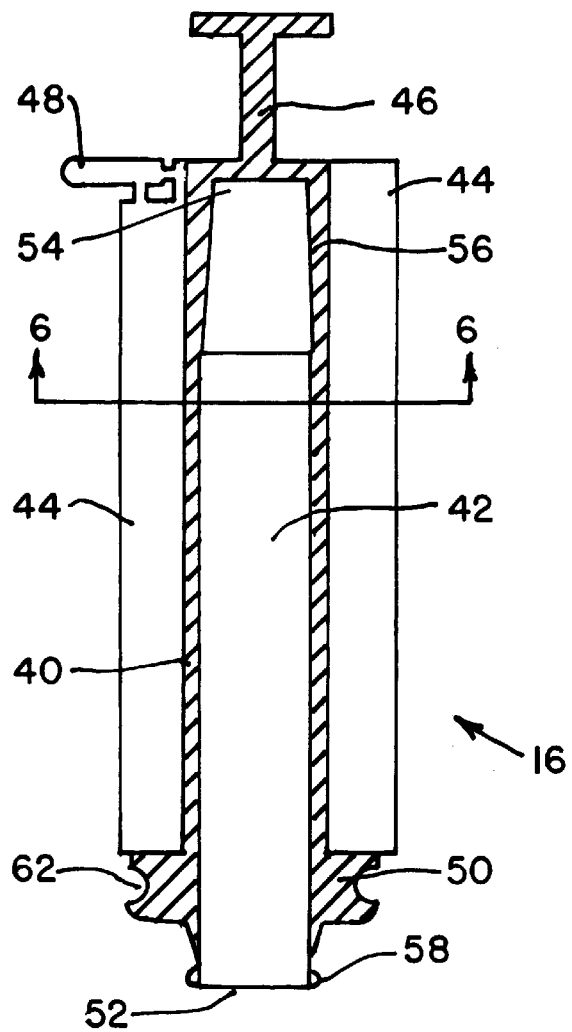
FIG. 5

FIG. 7
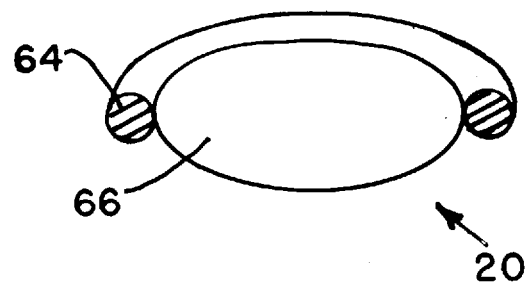
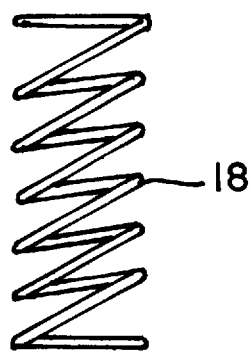
FIG. 8
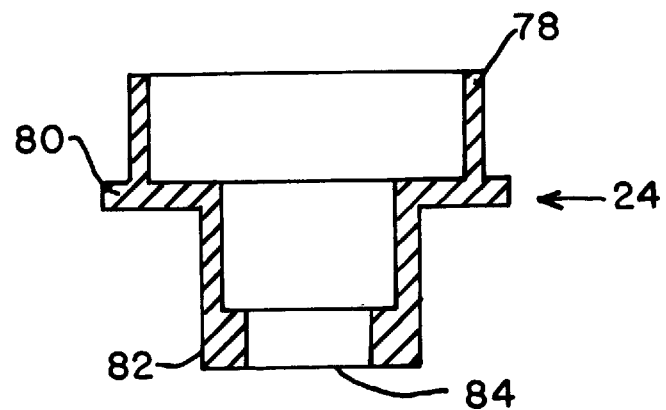
FIG. 9

HYPODERMIC SYRINGE WITH RETRACTABLE NEEDLE MOUNT

FIELD OF THE INVENTION

This invention relates to a hypodermic syringe and more particularly to a hypodermic syringe incorporating means for retracting a needle within the syringe and thereby preventing re-use of the syringe.

BACKGROUND OF THE INVENTION

Presently, there is considerable concern within the general public and within the medical profession relating to injuries or infections caused by accidental stabbing of a person by a needle affixed to a hypodermic syringe. Such injury or infection is commonly referred to as a "needle-stick injury". This type of injury arises because hypodermic syringes currently in use are provided with needles which are exposed before and after use of the hypodermic syringe. Capping or shielding of needles can be employed. However, needle-stick injuries can occur during recapping or reshielding after the syringe has been used. For this reason recapping is forbidden in many medical institutions. Additionally, re-use of a used syringe exposes persons to the risk of infection.

A number of solutions to the problems caused by exposed needles on used syringes have been advanced. For instance, Australian Patent Application No. 628814 discloses a hypodermic syringe having a retractable needle carried in a needle support mounted on the end of the syringe body, the needle being attached to a needle holder which has a conical head on the end distant from the point of the needle. A passage in the needle holder enables communication between the needle bore and the chamber of the syringe through holes in the needle holder. The piston has a sealing cap engaged therewith and also a forwardly extending tubular portion defining an opening with a tapered wall which engages over the conical edge of the needle holder to lock the head behind an abutment surface when the piston is pushed in. At the same time a diaphragm formed by the sealing cap extending across the tubular portion of the piston is ruptured so that the chamber of the syringe is no longer sealing the enclosed. Withdrawal of the piston and the associated plunger draws the needle into the chamber. The needle can then be received into a housing within the body of the plunger. This approach was perceived as addressing or overcoming disadvantages seen in the complexity of arrangements such as those disclosed in the U.S. Pat. Nos. 4,779,655, 4,710,170, 4,675,005, 4,650,468, 4,592,744 and 4,507,117.

However movement of the piston away from the closed end of the body of the syringe is necessary if the needle is to be drawn into the chamber of the syringe. Prior to this manoeuvre being completed the potential for needle-stick injury is still real. Additionally, further movements are required to effect receival of the needle into the housing provided in the body of the plunger of the piston.

Other solutions have been proposed in International Patent Application No. PCT/ES90/00002, U.S. Pat. No. 5,049,133, U.S. Pat. No. 4,838,869, U.S. Pat. No. 4,966,593, International Application No. PCT/FR90/00656, and Australian Patent Applications 57097/90 and 39180/89. However, these specifications concern themselves with what are called "fixed needle" syringes. The needles on these syringes are not capable of being interchanged to take different requirements into account. Further, the syringes have an appreciable number of components, leading to relatively high manufacturing costs.

The present invention seeks to provide a hypodermic syringe which will be useful in reducing needle-stick injury and which will permit interchanging of needles to meet varying requirements.

The present invention also seeks to provide a hypodermic syringe which, after use, cannot be re-used.

The present invention also seeks to provide a hypodermic syringe which is economical to manufacture and has a small number of components.

Other objects, advantages or features of the present invention as set forth in the following description all will become apparent by practice of the present invention.

DESCRIPTION OF THE INVENTION

According to one aspect of the present invention there is provided a hypodermic syringe comprising a barrel for containing medicament or other liquid, piston means movable within said barrel between a first end and a second end thereof, needle mounting means disposable within said barrel, means for imparting movement to said needle mounting means, restraining means located towards said first end, said needle mounting means when in a first position having a portion thereof extending from said first end and being restrained from movement by engagement with said restraining means, said restraining means being operable to release said needle mounting means when said piston means approaches said first end and then to engage and restrain from reverse movement said piston means, said piston means having a shaft provided with a chamber capable of receiving and retaining said needle mounting means and frangible sealing means to seal said chamber, wherein said needle mounting means, when released, is propelled from said first position to a second position wherein it is received and retained within said chamber after passing through said frangible sealing means.

Preferably said means for imparting movement is a spring under compression. More preferably the spring is a coil spring.

The portion of the needle mounting means, or "shuttle", that extends from the barrel terminates in a taper on which interchangeable needles can be seated. Preferably the taper is an international standard taper. In use a needle, being firmly seated on the taper, consequently is conveyed into the chamber in the shaft of the piston means along with the shuttle when the shuttle is released.

Preferably the walls of the chamber in the shaft of the piston means are so shaped as to engage the shuttle in a firm holding relationship when the shuttle is propelled into the chamber. More preferably the longitudinal wall or walls of the chamber is or are so geometrically configured that the shuttle is held fast in a jamming relationship after it has been propelled into the chamber.

The restraining means is integral with the barrel and preferably takes the form of an annular structure extending inwardly of the inner wall of the barrel. More preferably the annular structure contains a plurality of radially-extending weakened portions, which are fractured by forces exerted by means provided on the piston means. Still more preferably the restraining means engages the piston means after release of the shuttle in such a manner that the piston means cannot be withdrawn without causing further damage to the restraining means.

Preferably, means are provided to prevent premature or accidental release of the shuttle. Such means can take the form of a detachable lug on the shaft of the piston means capable of engaging a portion of the barrel (preferably the second end) and thereby limiting the range of movement of the piston means towards said first end and preventing said piston means from operating said restraining means.

DESCRIPTION OF PREFERRED EMBODIMENTS

In order that the invention may be more clearly understood and readily put into effect a preferred non-limiting embodiment is now described with reference to the accompanying drawings in which FIG. 1 is a longitudinal sectional view through a preferred embodiment of the invention prior to release of the shuttle;

FIG. 5 is a longitudinal sectional view of the piston means of the embodiment;

FIG. 6 is a cross-sectional view of the piston means along line C—C of FIG. 5;

FIG. 7 is a partially cut away perspective view of the frangible sealing means;

FIG. 8 is a spring being the movement imparting means;

FIG. 9 is a longitudinal sectional view of an end cap for the barrel;

Figure 1:
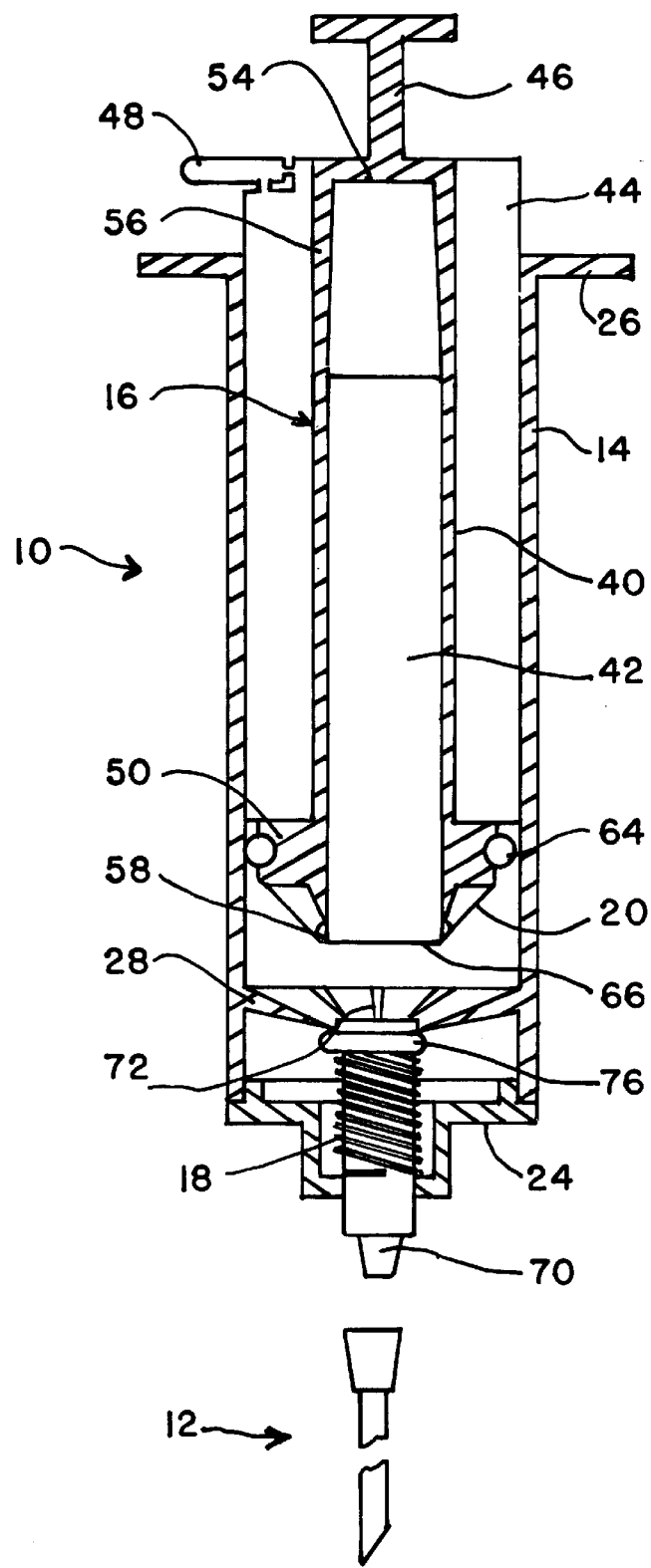

In the drawings the numeral 10 generally designates a preferred hypodermic syringe and the numeral 12 generally designates a hollow bore needle. Numeral 14 designates the barrel of the hypodermic syringe, numeral 16 designates the piston means, numeral 18 designates the spring, numeral 20 designates the sealing means, numeral 22 designates the shuttle, and numeral 24 designates the end cap.

The barrel 14 is a one piece moulding incorporating a finger grip 26 and a shuttle retainer 28, forming the restraining means, located close to open first end 30. The first end is closed off by end cap 24 while the open second end 32 receives piston means 16. The annular disc-like shuttle retainer 28 takes the form of a truncated hollow cone the apex of which is directed towards first end 30. The centre 34 of the shuttle retainer is open and the annulus 36 is provided with a plurality of radially-extending weakened portions 38.

The piston means 16 is also a one piece moulding comprising a shaft 40 defining a chamber 42, centralising fins 44, a thumb pad 46, a snap-off lock pin 48, and trigger and locking means 50. The lower end 52 of chamber 42 is open and can be sealed by frangible sealing means 20. The upper end 54 of chamber 42 is closed and the wall 56 of the chamber 42 adjacent upper end 54 is tapered inwardly. This is to provide a firm engagement with the shuttle 22 when it has been impelled into chamber 42 on its release from the shuttle retainer 28. The centralising fins 44 serve to keep the piston means 1 6 oriented correctly within barrel 14. The snap-off lock pin 48 is integral with one of the centralising fins 44 and here takes the form of a radially extending tab which engages the finger grip 26 of the barrel 14 and prevents the piston means 16 being pushed further into the barrel 14 towards first end 30. The snap-off lock pin 48 can be readily snapped off when required. The trigger and locking means 50 are designed so that in use annular shoulder 58 engages upper surface 60 of shuttle retainer 28 as the piston means 16 is fully depressed. The piston means 16 is also provided with annular depression 62 to receive the O-ring 64 of frangible piston sealing means 20, the frangible diaphragm 66 of which covers open lower end 52.

The piston sealing means 20 is a one-piece neoprene type moulding with the frangible diaphragm 66 being of such a thickness that it provides a satisfactory seal for chamber 42 and yet can be pierced readily by piercing means provided on the shuttle 22. The O-Ring 64 abuts the inner wall of barrel 14 in a sealing relationship.

Shuttle 22, which is a one-piece moulding, comprises a shaft 68 with bore 74 along the longitudinal axis thereof. One end of shaft 68 terminates in a standard taper 70 which can receive complementary hollow needle 12 and the other end of the shuttle is provided with spike means 72 for piercing the frangible diaphragm 66. Spike means 72 comprises a part-cone partly bounding bore 74 and permits communication between the bore 74 and the inside of the barrel 14. An annular shoulder 76 is disposed round the shuttle adjacent to the upper end. This annular shoulder 76 is engaged by the shuttle retainer 28 as is shown in FIG. 1 and also prevents the shuttle retainer falling out of the syringe through the end cap.

One-piece moulding end cap 24 is provided with a cylindrical wall 78 and annular flange 80 so sized as to permit it to be seated securely on the first end of barrel as is shown in FIG. 1. During assembly of the syringe heat welding or suitable adhesives may be used to fix the end cap in place. Shoulder 82 acts as a seat for spring 18 as is shown in FIG. 1. Bore 84 is so sized as to permit inward passage of portion of shaft 68 and needle 12 mounted on the shuttle.

The spring 18 is formed from surgical quality steel and is capable of exerting force sufficient to drive the shuttle 22 firmly into the tapered upper portion of the chamber 42 defined by wall 56. The other components may be constructed from any suitable material or combinations of materials. As can be seen, a hypodermic syringe according to the present invention has a small number of components, thereby lessening manufacturing costs.

Figure 2:
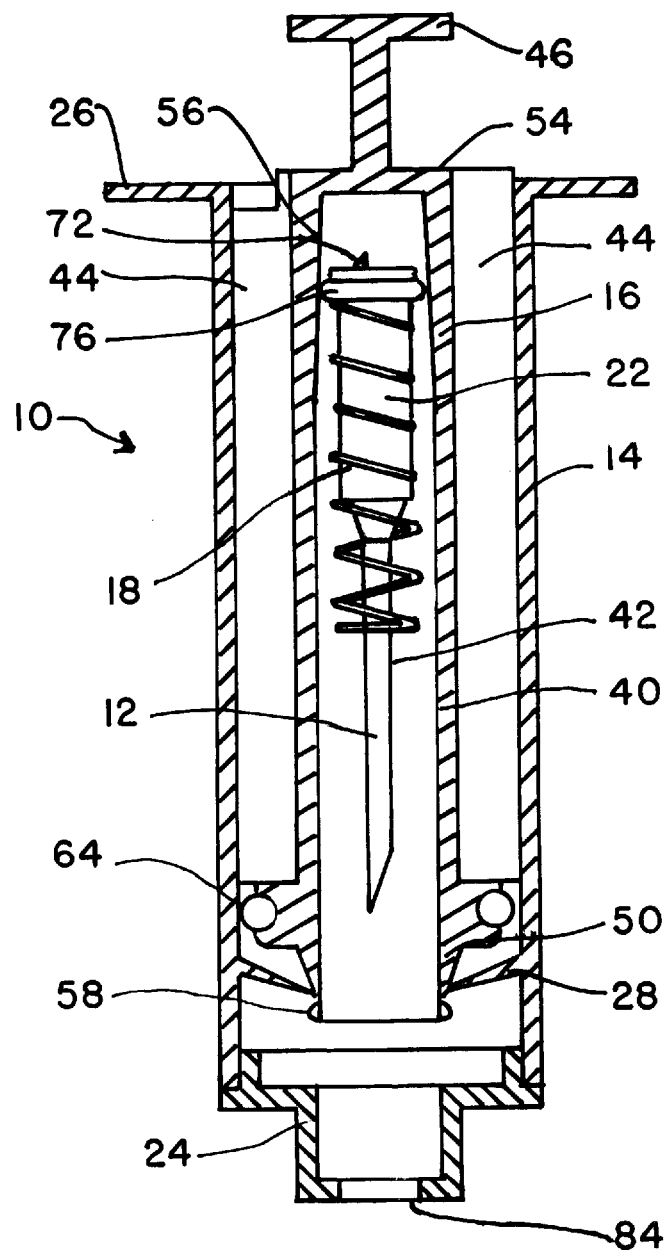
FIG. 2 is a longitudinal sectional view of the embodiment of FIG. 1 after release of the shuttle.
Figure 3:
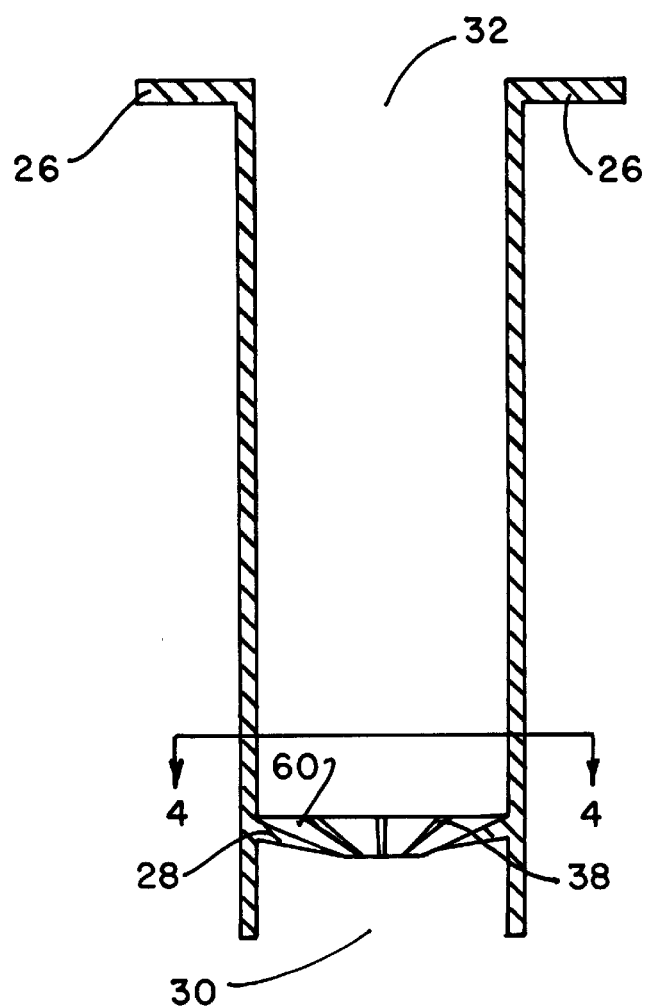
FIG. 3 is a longitudinal sectional view of the barrel of the embodiment.
Figure 4:
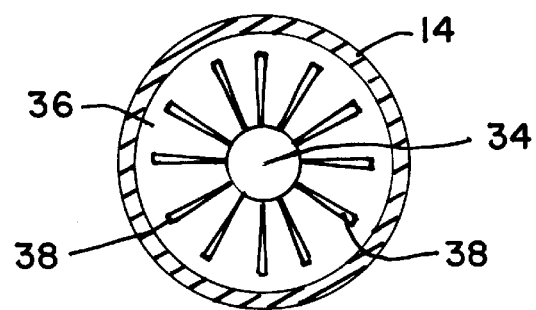
FIG. 4 is a cross-sectional view of the barrel along line A—A of FIG. 3.
Figure 10:
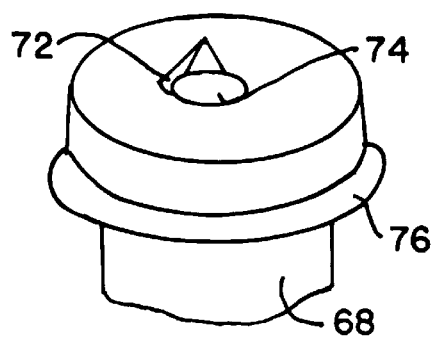
FIG. 10 is a perspective view of the upper part of a shuttle.
Figure 11:
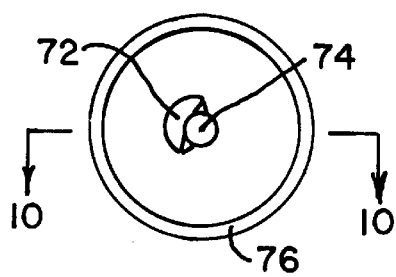
FIG. 11 is a top plan view of the shuttle of FIG. 10.
Figure 12:
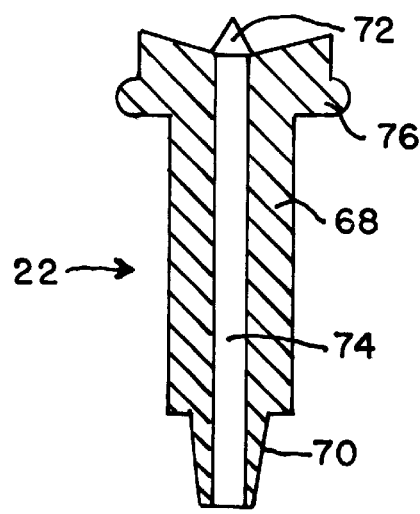
FIG. 12 is a longitudinal sectional view of the shuttle along line D—D of FIG. 11.

In use a selected needle is mounted on the taper of the shuttle and the barrel is filled in a conventional manner by drawing out the piston means. After filling is complete and the required dose is obtained, the snap-off lock pin 48 is broken off and the injection is given. During the completion of the injection stroke the following occurs in sequence:

(a) the spike means 72 on the shuttle 22 pierces the frangible diaphragm 66;

(b) the lower end 52 of the piston means 16 engages the upper surface 60 of the shuttle retainer 28 and fractures the annulus 36 along the plurality of radially-extending weakened portions 38;

(c) the lower end 52 of the piston means 16 spreads the "leaves" so formed, thereby disengaging them from the annular shoulder 76 of shuttle 22 and permitting the shuttle 22 with needle 12 attached to be propelled into the chamber 42 of the piston means 16 with such force that the shuttle 22 is jammed into the tapered upper portion of the chamber 42 defined by wall 56 and held there;

(d) the lower end 52 of the piston means 16 passes through the "leaves" which then spring back over the top of the small annular shoulder 58 and engage it thereby restraining withdrawal of the piston means 16, as shown in FIG. 2.

The hypodermic syringe and needle cannot be reused as the shuttle retaining means has been fractured and the shuttle and needle have been caught within the chamber in the piston means. The piston means cannot be withdrawn without further destruction of the shuttle retaining means.

It is believed that the invention and many of its attendant advantages will be understood from the foregoing description and it will be apparent that various changes may be made in the form, construction, and arrangement of the hypodermic syringe and the changes may be made in the form, construction and arrangement of the preferred embodiment described without departing from the spirit and scope of the invention or sacrificing all of its material advantages.

We claim:

1. A hypodermic syringe as comprising a barrel for containing medicament or other liquid, piston means movable within said barrel between a first end and a second end thereof, needle mounting means disposable within said barrel, means for imparting movement to said needle mounting means, restraining means located towards said first end, said needle mounting means when a first position having a portion thereof extending from said first end, said extending portion being provided with a taper on which an interchangeable needle can be seated, said needle mounting means being restrained from movement by engagement with said restraining means, said restraining means being integral with said barrel and taking a form of an annular structure extending inwardly of the inner wall of the barrel, said annular structure containing a plurality of radially-extending weakened portions, which may be fractured by force exerted by means provided on said piston means, and being operable to release said needle mounting means when said piston means approaches said first end and then to engage and restrain from reverse movement said piston means, said piston means having a shaft provided with a chamber capable of receiving and retaining said needle mounting means and frangible sealing means to seal said chamber, wherein said needle mounting means, when released, is propelled from said first position to a second position wherein it is received and retained within said chamber after passing through said frangible sealing means, wherein said annular structure contains a plurality of radially-extending weakened portions, which may be fractured by forces exerted by means provided on said piston means.

2. A hypodermic syringe as claimed in claim 1 wherein said restraining means engages said piston means after release of said needle mounting means so that said piston means cannot be withdrawn from said first end of the hypodermic syringe without causing damage to said restraining means.

3. A hypodermic syringe as claimed in claim 1 wherein said restraining means engaged said piston means after release of said needle mounting means so that said piston means cannot be withdrawn from said first end of the hypodermic syringe without causing damage to said restraining means.

4. A hypodermic syringe as claimed in claim 1 wherein said means for imparting movement is a spring under compression.

5. A hypodermic syringe as claimed in claim 1 wherein the walls of said chamber are so shaped as to engage said needle mounting means in a firm holding relationship when said needle mounting means has been propelled into said chamber.

6. A hypodermic syringe as claimed in claim 5 wherein said firm holding relationship is a jamming relationship.

7. A hypodermic syringe as claimed in claim 1 wherein means are provided to prevent premature or accidental release of said needle mounting means.

8. A hypodermic syringe as claimed in claim 7 wherein said means to prevent premature or accidental release comprise a detachable lug provided on the shaft of the piston means, said detachable lug being capable of engaging of the second end of said barrel and thereby limiting the range of movement of the piston means towards said first end.

9. A hypodermic syringe comprising a barrel for containing medicament or other liquid, piston means movable within said barrel between a first end and a second end thereof, needle mounting means disposable within said barrel, means for imparting movement to said need mounting means, restraining means located towards said first end, said needle mounting means when in a first position having a portion thereof extending from said first end, said extending portion being provided with a taper on which an interchangeable needle can be seated, said needle mounting means being restrained from movement by engagement with said restraining means, said restraining means being integral with said barrel and taking a form of an annular structure extending inwardly of the inner wall of the barrel, said annular structure containing a plurality of radially-extending weakened portions, which may be fractured by forces exerted by means provided on said piston means, and being operable to release said needle mounting means when said piston means approaches said first end and then to engage and restrain from reverse movement said piston means, said piston means having a shaft provided with a chamber capable of receiving and retaining said needle mounting means and frangible sealing means to seal said chamber, wherein said needle mounting means, when released, is propelled from said first position to a second position wherein it is received and retained within said chamber after passing through said frangible sealing means; wherein said restraining means engages said piston means after release of said needle mounting means so that said piston means cannot be withdrawn from said first end of the hypodermic syringe without causing damage to said restraining means.

10. A hypodermic syringe as claimed in claim 9 wherein said means for imparting movement is a spring under compression.

11. A hypodermic syringe as claim in claim 9 wherein the walls of said chamber are so shaped as to engage said needle mounting means in a firm holding relationship when said needle mounting means has been propelled into said chamber.

12. A hypodermic syringe as claimed in claim 11 wherein said firm holding relationship is a jamming relationship.

13. A hypodermic syringe as claimed in claim 9 wherein means are provided to prevent premature or accidental release of said needle mounting means.

14. A hypodermic syringe as claimed in claim 13 wherein said means to prevent premature or accidental release comprise a detachable lug provided on the shaft of the piston means, said detachable lug being capable of engaging of the second end of said barrel and thereby limiting the range of movement of the piston means towards said first end.

\* \* \* \* \*

UNITED STATES PATENT AND TRADEMARK OFFICE
CERTIFICATE OF CORRECTION

PATENT NO. : 5,843,034
DATED : Dec. 1, 1998
INVENTOR(S) : REDFERN, et. al.

It is certified that error appears in the above-identified patent and that said Letters Patent is hereby corrected as shown below:

On the title page, the following assignee data should be deleted:
"[73] Assignee: Lok-Tek International Ltd., Australia".

Signed and Sealed this

Twenty-sixth Day of October, 1999

*Attest:*

Q. TODD DICKINSON

*Attesting Officer*   *Acting Commissioner of Patents and Trademarks*